United States Patent
Barker

(10) Patent No.: US 11,399,585 B2
(45) Date of Patent: Aug. 2, 2022

(54) ANATOMICALLY TARGETED COMPRESSION CLOTHING

(71) Applicant: ANATOMIC FOCUS LIMITED, Surrey (GB)

(72) Inventor: Stephen George Edward Barker, Surrey (GB)

(73) Assignee: ANATOMIC FOCUS LIMITED, Surrey (GB)

( * ) Notice: Subject to any disclaimer, the term of this patent is extended or adjusted under 35 U.S.C. 154(b) by 322 days.

(21) Appl. No.: 16/541,644

(22) Filed: Aug. 15, 2019

(65) Prior Publication Data
US 2019/0365590 A1 Dec. 5, 2019

Related U.S. Application Data

(63) Continuation of application No. 14/804,990, filed on Jul. 21, 2015, now Pat. No. 10,420,694, which is a (Continued)

(30) Foreign Application Priority Data

Jan. 22, 2013 (GB) ..................... 1301116

(51) Int. Cl.
*A61F 13/08* (2006.01)
*A41D 13/00* (2006.01)
(Continued)

(52) U.S. Cl.
CPC ....... *A41D 31/185* (2019.02); *A41D 13/0015* (2013.01); *A41D 13/1236* (2013.01);
(Continued)

(58) Field of Classification Search
CPC ........ A61F 5/01; A61F 5/0104; A61F 5/0106; A61F 5/0109; A61F 5/012; A61F 5/30; A61F 13/00038; A61F 13/04; A61F 13/06; A61F 13/061; A61F 13/062; A61F 13/064; A61F 13/08; A61F 13/085; A61F 13/10; A61F 13/101; A61F 13/102; A61F 13/107; A61F 13/108; A61F 13/143;
(Continued)

(56) References Cited

U.S. PATENT DOCUMENTS 9,345,275 B2   5/2016  Albin et al.
10,420,694 B2 * 9/2019  Barker ............... A41D 13/0015
(Continued)

*Primary Examiner* — Ophelia A Hawthorne
(74) *Attorney, Agent, or Firm* — Saliwanchik, Lloyd & Eisenschenk

(57) ABSTRACT

An item of clothing is adapted to be worn against the skin, and having at least one panel adapted to provide targeted compression of at least 20% of the total length of a specific surface vein in the body, or adapted to provide targeted compression of at least 20% of a specific plexus of veins, a specific lymphatic plexus, drainage plexus or a collection of lymphatic vessels. The clothing is useful in a method of reducing recovery time in a human or other mammal, after a period of activity and in a method of enhancing performance, in particular sports performance, in a human or other mammal. It may also improve the conditioning of the skin and aid lymphatic drainage, and can be used in the treatment of certain medical conditions.

17 Claims, 8 Drawing Sheets

Related U.S. Application Data continuation-in-part of application No. PCT/GB2014/050155, filed on Jan. 21, 2014.

(51) Int. Cl.

| | | |
|---|---|---|
| *A41D 31/18* | (2019.01) | |
| *A41D 13/12* | (2006.01) | |
| *A61F 13/14* | (2006.01) | |
| *A61H 1/00* | (2006.01) | |
| *A61H 7/00* | (2006.01) | |
| *A61F 7/02* | (2006.01) | |

(52) U.S. Cl.
CPC ............ *A61F 13/08* (2013.01); *A61F 13/143* (2013.01); *A61H 1/008* (2013.01); *A61H 7/001* (2013.01); *A41D 2400/82* (2013.01); *A61F 7/02* (2013.01); *A61F 2007/0233* (2013.01); *A61F 2007/0266* (2013.01); *A61H 2205/06* (2013.01); *A61H 2205/108* (2013.01); *A61H 2205/12* (2013.01)

(58) Field of Classification Search
CPC ...... A61F 2007/0233; A61F 2007/0234; A61F 2007/0236; A61F 2007/0266; A61F 2013/00119; A61F 2013/00131; A61F 2013/00327; A61H 1/008; A61H 7/001; A41D 13/0015; A41D 13/0017; A41D 13/1236; A41D 2400/38; A41B 11/02

See application file for complete search history.

(56) References Cited

U.S. PATENT DOCUMENTS

| | | |
|---|---|---|
| 2005/0113729 A1 | 5/2005 | Scott et al. |
| 2006/0169004 A1 | 8/2006 | Belluye et al. |
| 2007/0033696 A1 | 2/2007 | Sellier |
| 2008/0189829 A1 | 8/2008 | Fusco |
| 2009/0025115 A1 | 1/2009 | Duffy et al. |
| 2009/0113596 A1 | 5/2009 | Young et al. |
| 2010/0130903 A1 | 5/2010 | Rock |
| 2011/0035860 A1 | 2/2011 | Heel |
| 2011/0196416 A1 | 8/2011 | Lambertz |
| 2011/0203036 A1 | 8/2011 | Turner et al. |
| 2011/0208104 A1 | 8/2011 | Sellier |
| 2011/0302686 A1 | 12/2011 | Chapuis |
| 2012/0117702 A1 | 5/2012 | King |

\* cited by examiner

ANATOMICALLY TARGETED COMPRESSION CLOTHING

REFERENCE TO RELATED APPLICATIONS

This Application is a continuation of U.S. application Ser. No. 14/804,990, filed Jul. 21, 2015, which is a continuation-in-part of International Patent Application No. PCT/GB2014/050155, filed Jan. 21, 2014, which claims priority to Great Britain Patent Application No. 1301116.8, filed Jan. 22, 2013, the disclosures of which are incorporated herein by reference in their entireties.

FIELD OF THE INVENTION

The present invention relates to items of graduated compression or compression clothing, for example sportswear, and is particularly useful for enhancing one or more aspects of sports performance. The clothing also has utility in the medical field.

BACKGROUND TO THE INVENTION

Graduated compression hosiery has long been used in the medical industry, for example to aid in the prevention of deep vein thrombosis and as a means to help manage the post-thrombotic syndrome. In addition, graduated compression hosiery has known application for managing varicose veins and as used for everyday wear, it helps in terms of prevention of tired, swollen and generally uncomfortable legs, and especially with travel and with pregnancy.

Graduated compression clothing has also been trialled to aid with sports recovery after exercise but at present, the scientific and sports community give mixed reports of its efficacy for overall performance enhancement.

Non-graduated compression clothing is exemplified by forms of specialist swimwear and athletic wear. It is also used in extreme form by military pilots flying fast jets, whereby compression of the lower limbs forces blood to circulate maximally to the head, core and upper body to help prevent blackout.

The enhancement of overall sports performance is a worthwhile goal. A very small increment in sports performance is the difference between losing and winning a race, and thus a great deal of research is being done in the area. There are many items of clothing on the market that indirectly enhance performance, for example padded cycling shorts exist that make the rider more comfortable which therefore, may indirectly increase performance. Sports clothing can directly improve performance not as a result of the athlete's ability per se, but because of creating for example, less wind or water resistance through being worn tight and creating a more aerodynamic profile. On occasion, such materials technology can be deemed 'unfair' and can result in a ban of its use in professional sport as with for example, all-in-one, full body swim suits for use during previous Olympic Games.

There exists a need for an item(s) of clothing or other sportswear that can directly help enhance individual sports performance and/or sports recovery. This ability to aid in sport might well be translated to the medical industry, for example, to further improve the management of varicose veins, the post-thrombotic syndrome, lymphoedema, or quasi-medical conditions such as 'cellulite'.

SUMMARY OF THE INVENTION

The present invention is based on an understanding of human anatomy, and in particular angiology. It is also based on experiments, which have shown that targeted compression of specific surface veins or specific groups of surface veins when wearing an item of clothing is achievable. Furthermore, it is believed that the enhanced delivery of oxygenated blood to the tissues of a particular area is achievable, and that further indirect effects may be achieved, such as affecting the temperature of the skin.

The average human has approximately five litres of blood circulating around the whole of the body. At rest, it is estimated that 5%-8% of this total volume is contained within the skin and superficial venous system. With exercise and especially with vigorous exercise, and as a means to help with heat loss, the circulation to the skin can increase and surface veins can become visibly distended, to increase the total blood volume here up to 10% of the total blood volume.

It is well known in a number of sports, that training at altitude can have a significant, but temporary effect to enhance overall performance. The physiological principle here is that at altitude, the concentration of breathable oxygen in the atmosphere is reduced, causing the body to respond with an increased production of a hormone (erythropoietin) which in turn, leads to the increased production of oxygen carrying red blood cells. This enhanced ability to get oxygen to muscles and so, enhance athletic ability is retained for some time when the sportsperson in training, returns to 'ground level'. The same principle is present with the illegal use of synthetic (erythropoietin—EPO) hormones, taken as 'drugs' to enhance sports performance. Use of this technique could improve overall performance by an estimated 1%-3%, until the blood level returns to normal—often estimated at 60-90 days.

Without wishing to be bound by theory, it is believed that targeted compression of specific (named) superficial veins, venous and lymphatic plexuses, as in the present invention, drains 'surface' blood to the deep circulation and has the effect of keeping the vast majority of the total circulating blood volume available to the core and major muscle groups in the body—the same end effect to increase available oxygen to the muscles—the same effect as training at altitude.

It is important to note that this "targeted" compression has many advantages to general compression, and it is advantageous to compress specific surface veins in preference to other areas Again, without wishing to be bound by theory, when an item of clothing of the invention is worn when participating in a particular sports activity, for the duration of that activity, draining blood from the superficial to deep systems would cause no lasting problem. The possible effect however, would be an immediate increase in the improvement of overall performance (by an estimated 3% to 7%). The possible effect on any one event could be enhanced if the sportsperson was to continually use the device, over a period of time, with sustained training.

According to a first aspect, an item of clothing, adapted to be worn against the skin, and comprising at least one panel adapted to provide targeted compression of at least 20% of the total length of a specific surface vein in the body, or adapted to provide targeted compression of at least 20% of a specific plexus of veins, a specific lymphatic plexus, drainage plexus or a collection of lymphatic vessels.

According to a second aspect, a method of reducing recovery time in a human or other mammal, after a period of activity, comprises applying an item according to any preceding claim, to the body, before, during or after the period of activity.

According to a third aspect, a method of enhancing overall performance, in particular sports performance, in a human or other mammal comprises applying an item as defined above, to the body, before or during the period of increased performance is desired.

According to a fourth aspect, a method of protecting the skin and tissues from trauma, in a human or other mammal, comprises applying an item as defined above, to the body.

According to a fifth aspect, a method of cooling the skin during a period of activity, in a human or other mammal, comprises applying an item as defined above, to the body, before, during or after the period of activity.

According to a sixth aspect, a method of warming the skin during a period of activity, in a human or other mammal, comprises applying an item as defined above, to the body, before, during or after the period of activity.

According to a seventh aspect, a method of skin massage and/or a method of increasing local skin circulation, in a human or other mammal, comprises applying an item as defined above, to the body.

According to an eighth aspect, a method of aiding lymphatic drainage in the skin and subcutaneous tissue, comprises applying an item as defined above, to the body.

According to a ninth aspect, a method of preventing and/or treating a medical condition, in a human or other mammal, comprises applying an item as defined above, to the body.

DESCRIPTION OF PREFERRED EMBODIMENTS

According to the invention, an item of clothing is adapted to be worn against the skin, and comprises a panel or panels adapted to provide targeted compression of at least 20% of the total length of a named or specific surface vein in the body, or adapted to provide targeted compression to a specific plexus of veins, a specific lymphatic plexus, a specific drainage plexus, or a collection of lymphatic vessels.

The veins of the body are divided into two principal sets; superficial and deep. The superficial veins are situated close the surface of the body, while the deeper veins are located further from the surface of the skin, beneath fascial layers, in and around muscle and bone. Communication between these systems exists.

Figure 6:
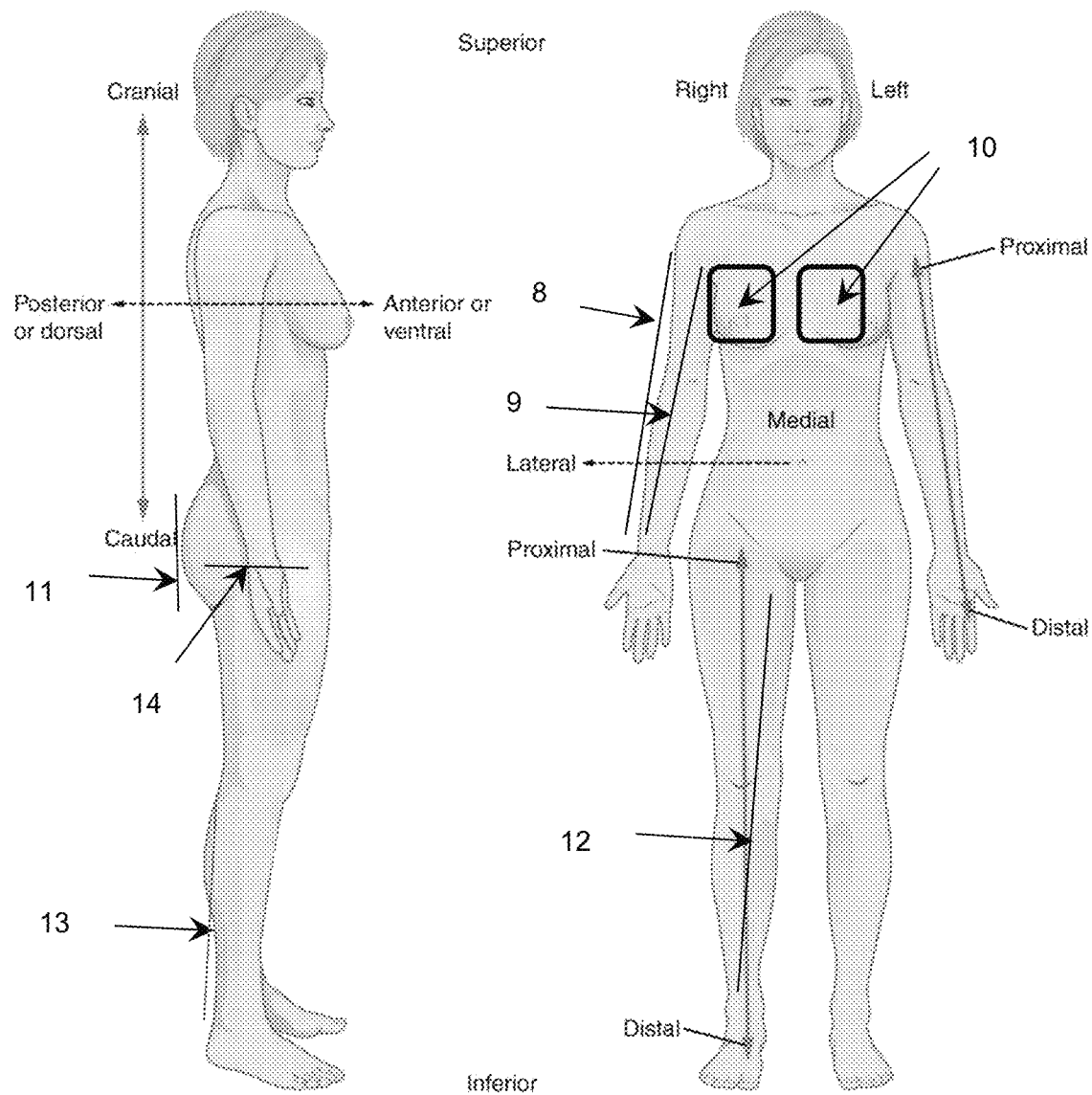
FIG. 6 is a schematic diagram showing areas of the body that can be compressed using an item of clothing according to the invention.

As used herein, the positions of the veins will be described relative to the body, when standing in the standard anatomical position. This position is depicted in FIG. 6. "Anatomical position" is a well-used term in the art, and describes the position that the body is in, when standing facing forward, with arms hanging to the sides and the palms of the hands facing forward, and the feet also facing forwards.

Figure 5:
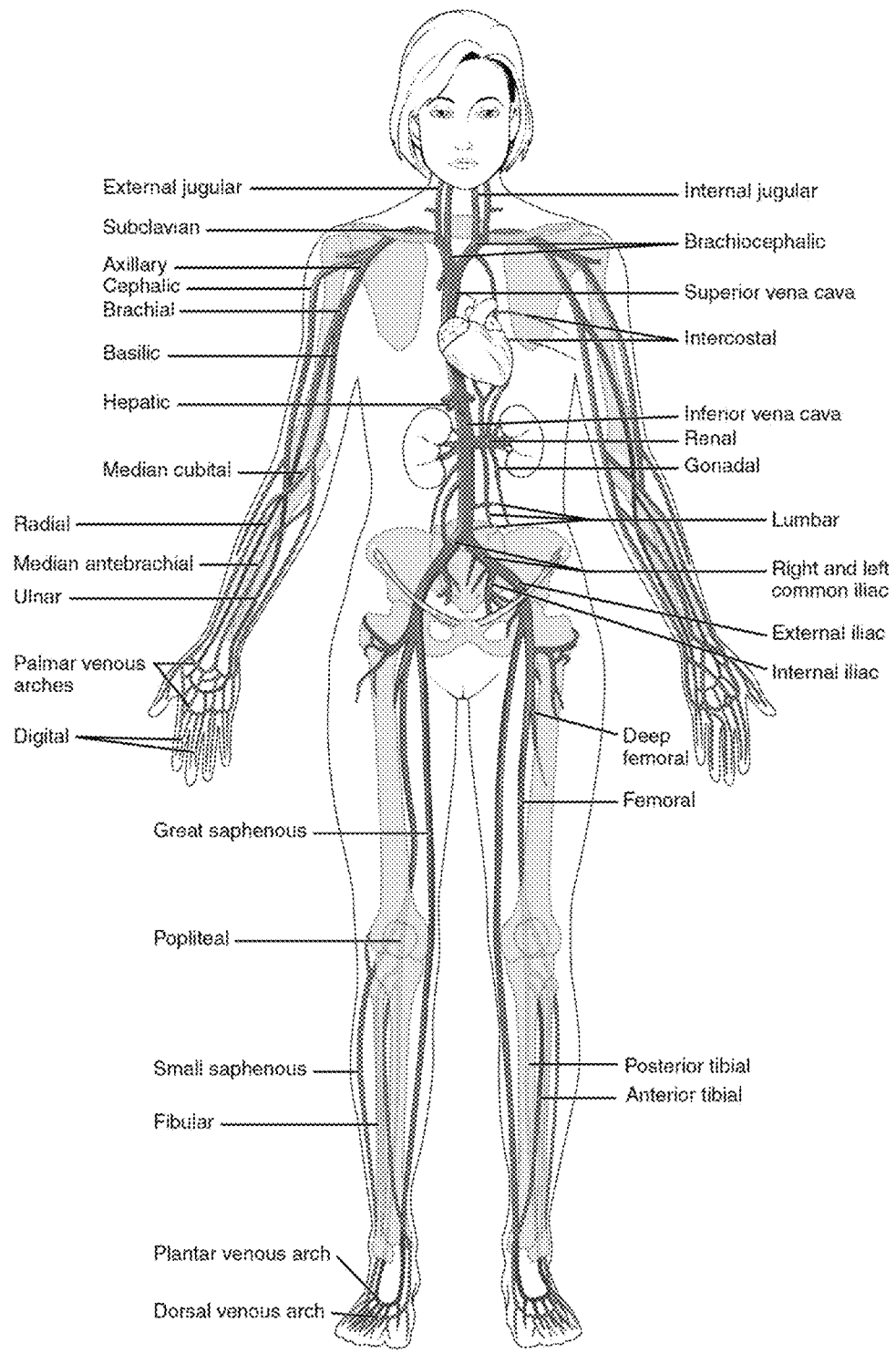
FIG. 5 is a schematic diagram showing the position of some of the major surface veins in the body.

FIG. 5 depicts the position of some of the named (specific) surface veins in the body. For example, the cephalic vein and the basilic vein are found in the arm. The cephalic vein is on the anterior lateral aspect of the arm and the basilic vein is on the anterior medial aspect of the arm. The superficial veins of the lower extremity are principally the long (or great) and short (or small) saphenous veins. The long saphenous vein is found along the more medial aspect of the leg and thigh and stretches almost the entire length of the limb. The short saphenous vein runs more along the posterior lateral aspect of the lower leg and terminates at or near the back of the knee.

There are also collections (plexuses) of drainage veins for example, in the buttocks and sides of the hips, and across the anterior chest wall overlying the pectoral muscles, which drain those regions.

In similar fashion, there are known lymphatic plexuses that drain specific superficial areas on the body. These plexuses in turn, drain in to lymphatic vessels that tend to run alongside the veins, especially in the lower and upper limbs.

These named (specific) surface veins, drainage plexuses or lymphatic plexuses, are situated in the fat layer between the skin and the fascia the covers the muscle. They run substantially parallel to the surface of the skin.

According to the present invention, the panel is adapted to apply targeted compression of at least 20% of the length of a named surface vein. It will be appreciated that the "length" of a specific vein lies substantially parallel to the surface of the skin.

According to the invention, the panel is adapted to apply targeted compression of at least 20% of a specific plexus. It will be appreciated that this can also be expressed as compression of at least 20% of the skin overlying a specific plexus.

An item of clothing of the invention may be an item of sportswear (for any sport), or an item intended for everyday wear. Included within the invention are items intended to be worn by professional sports people, as well as items intended to be worn by amateur sports people. The item of clothing may also be medical clothing, i.e. intended to have a therapeutic or condition-management effect. It may be available in a variety of different sizes, and for both sexes.

An item of clothing according to the invention may be for example, a t-shirt, long sleeved top, shorts, leggings, tights, ankle socks, or knee high socks.

An item of clothing according to the invention may be a swimsuit or a wetsuit.

An item of clothing of the invention is preferably an item of compression clothing. It may also be an item of graduated compression clothing.

A person skilled in the art will be able to make an item of clothing according to the invention. Having knowledge of basic anatomy, and of materials and methods for providing graduated or non-graduated compression, will enable the skilled person to carry out the invention.

As used herein, "panel" means, an area, or a region located on the item of clothing. It is preferably separate from and in addition to the material of the clothing. It may be retrofitted onto an item of clothing. The panel may be, for example, elongate, linear, square, oval or rectangular. The panel should be adapted to cover the vein, lymphatics or plexus that is to be compressed and the skilled person will be able to choose a suitable shape. The panel is preferably located on the inside, or on the inner layer of an item of clothing according to the invention, facing onto the skin. In this context, the word "panel" is a zone or an area within the clothing.

The item of clothing comprises a panel, or a plurality of panels, adapted to provide targeted compression of at least part of one or more of the surface veins, or to a plexus of veins, a lymphatic plexus or a lymphatic vessel(s), in the body.

The term "targeted compression" means that the area that is compressed is compressed preferentially, and to a larger degree than the non-targeted areas. In an item of clothing that comprises a panel adapted to provide targeted compression, to a region of the body in use, the area of the body that is directly in contact with the panel will be compressed preferentially compared to the area of the body that is not directly in contact with the panel. The area that is not directly in contact with the panel may either not be compressed at all, or may be compressed to a lesser degree, depending on the type of clothing (i.e. whether or not it is graduated compression or compression clothing).

In a preferred embodiment, when the panel(s) is adapted to provide targeted compression to a surface vein or to surface lymphatics, at least 20, 30, 40, 50, 60, 70, 80, 90 or up to 100% of the total length of the surface vein is targeted. Preferably, greater than 70% of the total length of the surface vein is targeted. A person skilled in the art will be able to pinpoint almost the entire length of these surface veins in the body.

In a preferred embodiment, when the panel(s) is adapted to provide compression to a plexus of veins or lymphatics, at least 20, 30, 40, 50, 60, 70, 80, 90 or up to 100% of the area of the skin covering the plexus is targeted. Preferably, greater than 70% of the area of skin covering the plexus is targeted.

In a preferred embodiment, the length of the panel(s) is from 5, 10 or 15 cm up to 20, 40, 60, 80, 100, 120, 140 or 150 cm, in one or multiple segments. Preferably, it is from 5 to 100 cm in length. The panel(s) may be continuous or discontinuous. For example, the panel may be in the form of a continuous pad. Alternatively, the panel may be in the form of an array of discrete pads/protrusions (15).

In a preferred embodiment, the width of the area of targeted compression is from 1, 2, 3, 4, or 5 cm up to 10, 20, 30, 40 or 50 cm, preferably 1 to 50 cm. In a preferred embodiment, the surface veins are selected for example from the cephalic vein, the basilic vein, the short saphenous vein and the long saphenous vein. The surface vein(s) may also be selected for example from the collection of drainage veins (plexuses) in the buttocks and sides of the hips, or across the anterior chest wall overlying the pectoral muscles, wherein the position of the drainage veins are described relative to the body when standing in the standard anatomical position.

When the panel is adapted to compress a named surface vein, it is not necessary for the panel to be very wide. However, it is also important that the panel is not made too narrow. This is because an item of clothing of the invention may not necessarily be custom-made, and the positions of the named surface veins vary to some degree in each individual. Therefore, the width of a panel of the invention should allow for these normal variances.

In a preferred embodiment, a panel or panels is adapted to cover most or the whole of the buttocks and sides of the hips, in use. Preferably, a panel is adapted to cover the greater part of the anterior chest wall, at least to the mid-line of the wearer, on both sides of the mid-line (the pectoral regions).

When the item of clothing is a short-sleeved or long-sleeved t-shirt, it preferably comprises two panels, each extending the length of each arm, i.e. each arm comprises two separate panels to provide targeted compression to the cephalic and basilic veins. The top may also comprise a panel(s) extending across the anterior chest wall, i.e. on the front of the garment to provide targeted compression to the respective pectoral venous plexuses.

When an item of clothing is adapted to provide compression to the basilic vein, the panel is preferably adapted to compress at least part of (preferably at least 30, 40, 50 or 60%) the anterior medial aspect of the arm (9), in use.

When an item of clothing is adapted to provide compression to the cephalic vein, the panel is preferably adapted to compress at least part of (preferably at least 30, 40, 50 or 60%) the anterior lateral aspect of the arm (8), in use.

When an item of clothing is adapted to provide compression to the lymphatic plexuses in the chest, the panel is preferably adapted to compress at least part of (preferably at least 30, 40, 50 or 60%) the anterior chest wall (10), in use.

When an item of clothing is adapted to provide compression to the lymphatic plexuses in the buttocks, the panel is preferably adapted to compress at least part of (preferably at least 30, 40, 50 or 60%) the buttocks (11) and lateral aspect of the hips (14), in use.

When an item of clothing is adapted to provide compression to the long saphenous vein, the panel is preferably adapted to compress at least part of (preferably at least 30, 40, 50 or 60%) the medial aspect of either the upper (proximal), lower (distal) or the entire leg (12), in use.

When an item of clothing is adapted to provide compression to the short saphenous vein, the panel (16) is preferably adapted to compress at least part of (preferably at least 30, 40, 50 or 60%) the posterio-lateral aspect of the lower leg (13), in use. When the item is a pair of trousers, leggings, or tights, it preferably comprises a panel on each inner (medial part of the) thigh, extending the length of the thigh, and down the inner (medial) aspect of each leg, so targeting the long saphenous vein. It preferably also comprises a panel extending over the buttocks and across to the sides of the hips, so targeting the respective venous plexuses. More preferably still, it comprises a panel extending from towards the back of the knee and down the outer (lateral) aspect of each leg, so targeting the short saphenous vein.

Preferably, the panel(s) is also adapted to compress a lymphatic plexus or plexuses, or a known principal set of lymphatic vessels. In practice, a panel(s) that compresses a surface vein will also compress a number of principal lymphatic vessels, as the lymphatic vessels commonly run alongside the surface veins especially in the arms and legs.

The panel(s) may be of any suitable material, e.g. compressed fluff fibre, silicone, latex rubber, a memory foam, polyurethane foam, firmer plastic or metal studs, or any combination thereof. In particular, it may be fashioned from printable polymer formulations already in use in the clothing industry.

Preferably, the pads or protrusions of the panel may be solid or semi-solid, or may be built up by depositing a suitable plastics or other material, e.g. by ink-jet printing, or by the application of pre-made transfers.

A panel of the invention is preferably formed from screen-printed polymer (preferably using tested, safe industry compounds). The pads are preferably formulated and shaped to be comfortable against the skin whilst interacting directly with it.

By way of example, the panel may be made up from an array or series of pads (protrusions) (15), optionally of differing sizes and/or of differing heights, arranged in such a way as to cover the known sites of surface veins and even more preferably to provide targeted compression on a background of graduated compression (i.e. the panel is applied/integrated with an item of graduation compression clothing). One advantage of having such an array of pads (15) is to allow greater movement of the 'compression zone' on the underlying garment substrate and to allow some 'breathability' between each pad (15).

Preferably, the item of clothing additionally comprises at least one region adapted to provide compression, preferably graduated compression, to the body, in use. More preferably, the basic item of clothing is an item of compression or graduated compression clothing, for example, the material from which the item of clothing is made is inherently resilient and "stretchy, e.g. Lycra™ (elastane). More preferably, the area adapted to provide targeted compression is superimposed on a region of graduated compression, i.e. the targeted compression is provided on a background of graduated compression. It may also be provided on a background of standard compression. This may be achieved by the item of clothing being made from a material adapted to provide compression, for example strong Lycra™ (elastane) with nylon, with a panel disposed on the inside thereof. The strength or weave of the Lycra™ may be varied throughout the item to provide graduated compression.

Preferably, the graduated compression is such that the greater compression levels are more distal from the heart and the lesser compression levels are more proximal to the heart, when the item is in use.

Preferably, the area adapted to provide targeted compression comprises a plurality of protrusions, projecting inwardly towards the skin surface, such that they act on the body, in use.

In a preferred embodiment, the heights of the protrusions e.g. pads, are varied in order to form an overall inward bulge, such that the focused compression is greatest in the centre of the panel. The location of the panel may be configured such that the centre of the panel targets the skin overlying the specific surface vein. The heights of the protrusions however, may be of uniform size.

Preferably, the area of targeted compression is adapted also, to help reduce the magnitude of any force acting externally thereon. This may have the effect to help prevent damage to the underlying skin, and may help minimize skin surface grazing and subcutaneous bruising. This may be achieved by varying the thickness of the panel and/or the materials from which the panel is constructed.

In a preferred embodiment, the panel is adapted to provide a region of insulation, which may help keep the skin surface warm during a period of activity, or in juxtaposition to this, help to provide a region of skin cooling, which may aid in the dissipation of heat and sweat. This may be achieved by varying the height and/or separation of the protrusions and/or the material from which they are made. Varying the material from which the item is made may also control the temperature effects on the body. Such temperature effects may also be influenced by whether the space created around the panel, between the skin and the item of clothing contains air, or water, or another substance.

In a preferred embodiment, the panel may also provide a region of both insulation, and skin cooling, depending on the surface temperature of the wearer of the item of clothing. From initial results obtained, it appears that during periods of relatively low activity, the garment may aid skin cooling, whereas during periods of high activity, the garment may provide a heating effect to the body. These may either directly or indirectly help enhance sports performance.

Preferably, the protrusions are between 100 microns and 10 mm high. More preferably, they are between 1 mm and 5 mm high. Preferably, the protrusions are in the form of a regular array. Alternatively, the protrusions may be in the form of a discontinuous array that form overall a suitable shape to effect targeted compression along the anatomically defined path of a specific superficial vein, or to cover an area that corresponds to a known venous or lymphatic plexus.

Preferably, the panel is configured as an inward bulge, such that within the area of targeted compression, there is a higher level of compression at the centre thereof, relative to the edges of the panel, i.e. the targeted compression is also sub-graduated. This may be achieved by having a graduated height of protrusions within the panel, such that the highest protrusions are in the centre of the panel, and the lowest protrusions are at the edge of the panel.

There are potentially many other benefits to the invention. One such benefit is that a panel may also have a "massage" effect on the skin, thus stimulating lymphatic drainage and/or reducing (the quasi-medical condition known as) cellulite and/or improving local skin blood flow.

The invention will now be further described with reference to the accompanying Figures. The Figures illustrate preferred embodiments of the invention.

Figure 1:
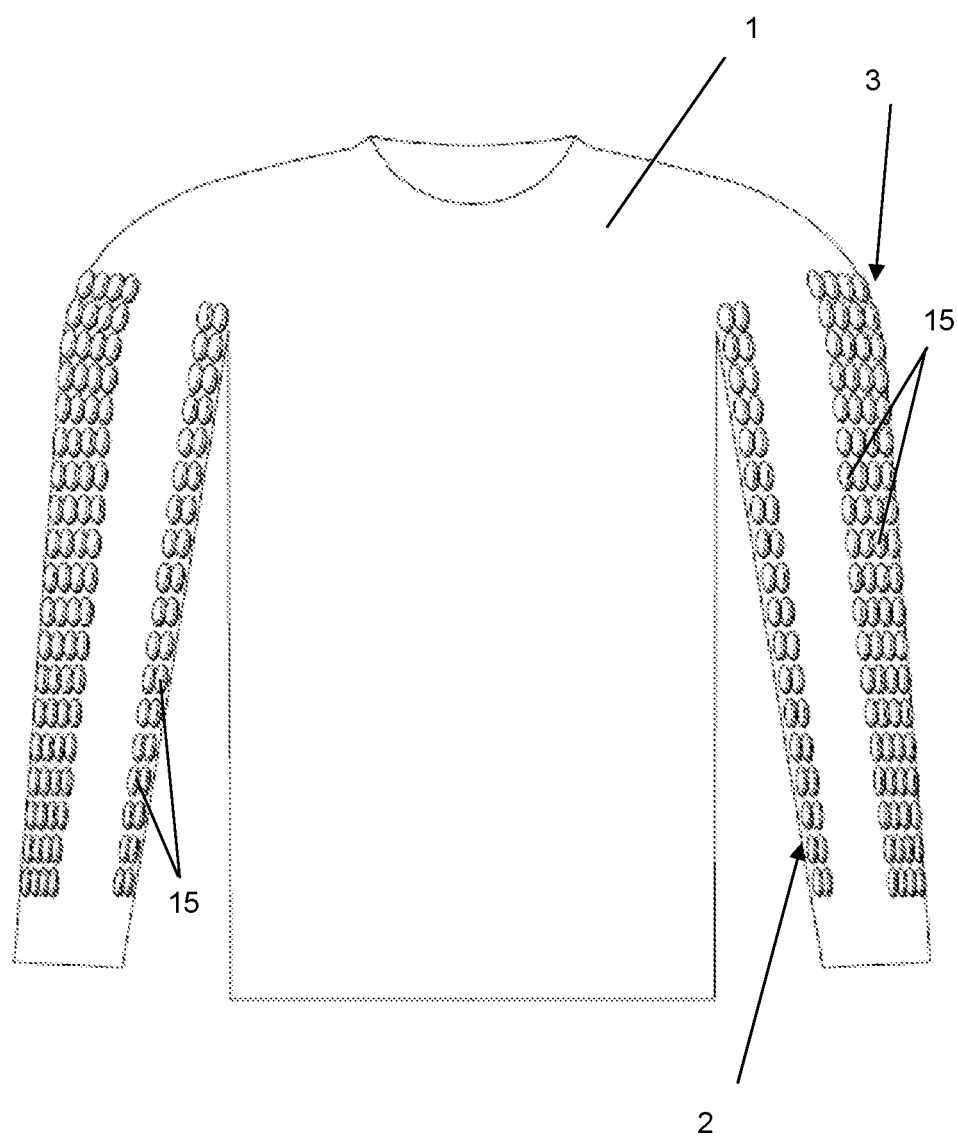
FIG. 1 is a front view of an example of a long-sleeved top according to the invention. The top is shown turned inside-out, i.e. in use the pads project inwardly towards the skin.
Figure 2:
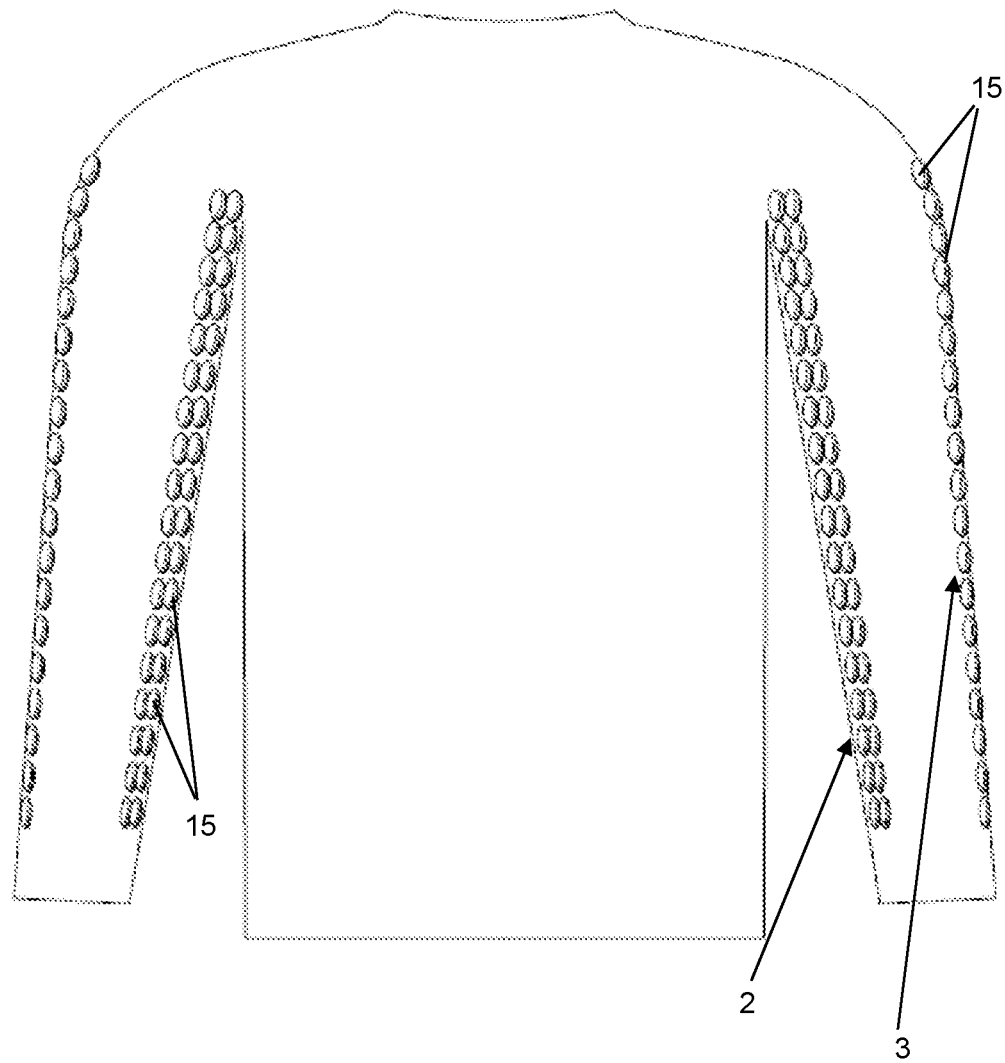
FIG. 2 is a back view of the top shown in FIG. 1.

FIGS. 1 and 2 illustrate the invention by showing a long-sleeved top (1) according to the invention. FIG. 1 shows the front of the top, and FIG. 2 shows the back. The top is shown inside-out. Each sleeve has two elongate panels on the inner surface, extending the length of the arm with 'pads' to provide targeted compression. One panel (2) targets the basilic vein and another panel (3) targets the cephalic vein.

Figure 3:
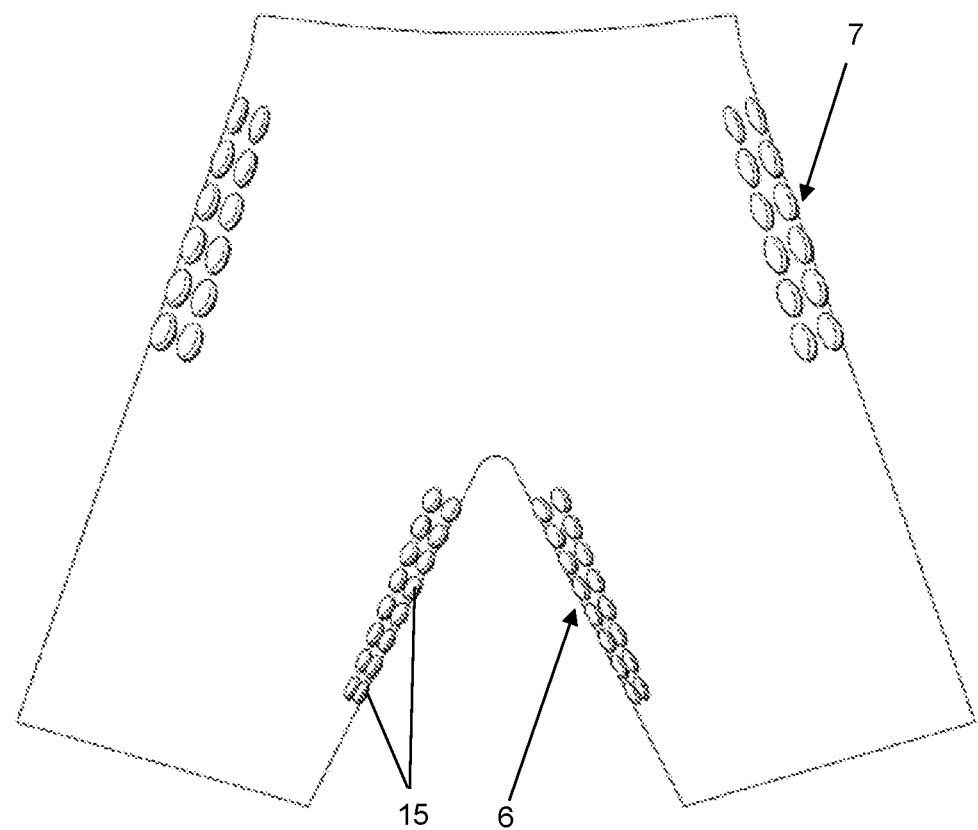
FIG. 3 is a front view of an example of a pair of shorts according to the invention. The shorts are shown turned inside-out, i.e. in use the pads project inwardly towards the skin.
Figure 4:
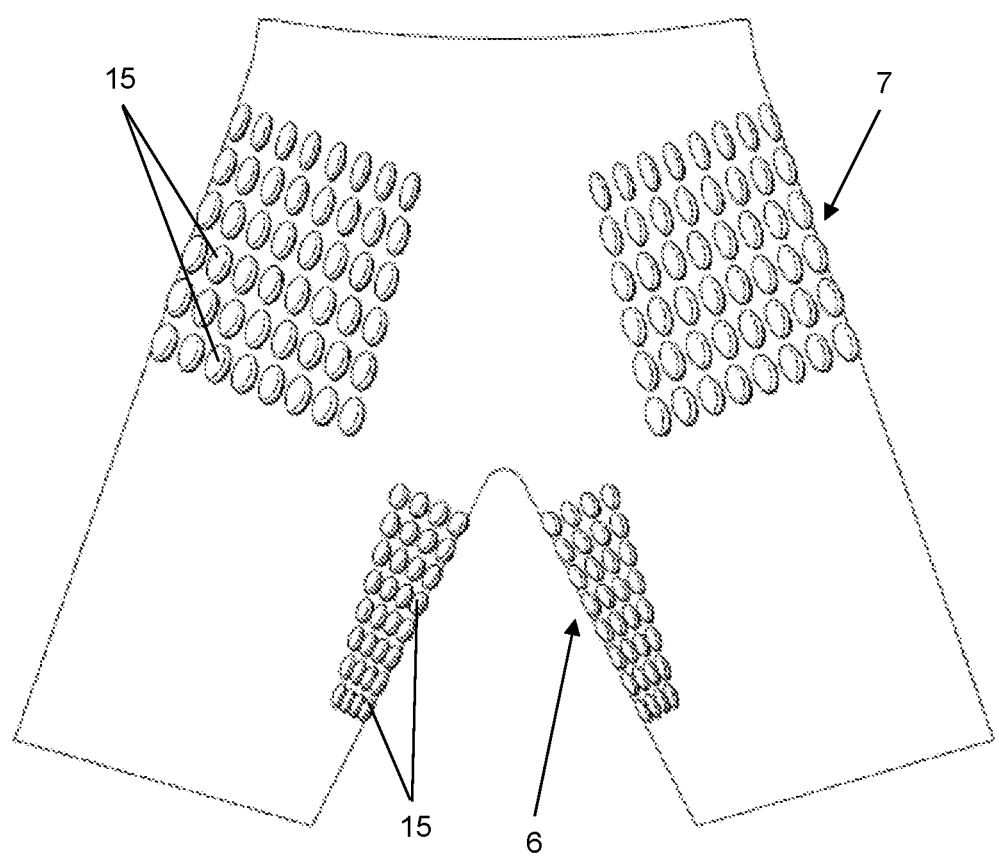
FIG. 4 is a back view of the shorts shown in FIG. 3.

FIGS. 3 and 4 show a pair of shorts according to the invention. They are shown inside-out. The shorts comprise a panel on each inner thigh (6), extending along part of the length of the thigh to target compression to the respective part of the long saphenous vein, and a panel (7) extending over the buttocks and across to the sides of the hips to target compression to the respective venous plexuses. This preferred embodiment is shown in FIGS. 3 and 4. FIG. 3 shows the anterior aspect of a pair of shorts, and FIG. 4 shows the posterior aspect of a pair of shorts, with 'pads' in place to provide targeted compression.

The following Studies illustrate the invention.

Study 1

A panel comprising an array of pads (protrusions) was integrated into an item of graduated compression hosiery. A clinical trial was undertaken and the item of hosiery was shown to aid in recovery after vigorous exercise and to enhance the delivery of oxygenated blood to the skin and tissues beneath.

The panels were shown to produce a 'focus of compression' on a background of graduated compression, so as to be able to flatten specific anatomical features in the subcutaneous tissues (e.g. the long or short saphenous veins in the legs) that results in the re-direction of blood flow to the deep veins which in turn, fully optimizes the return of blood back to the heart and lungs.

A panel according to the invention has been applied to compression leggings, shorts and t-shirts, to target body-wide specific anatomic features so as to enhance overall performance, recovery, body shape, skin tone and feel, and to aid in the prevention of certain conditions such as cellulite.

Study 2

Figure 7:
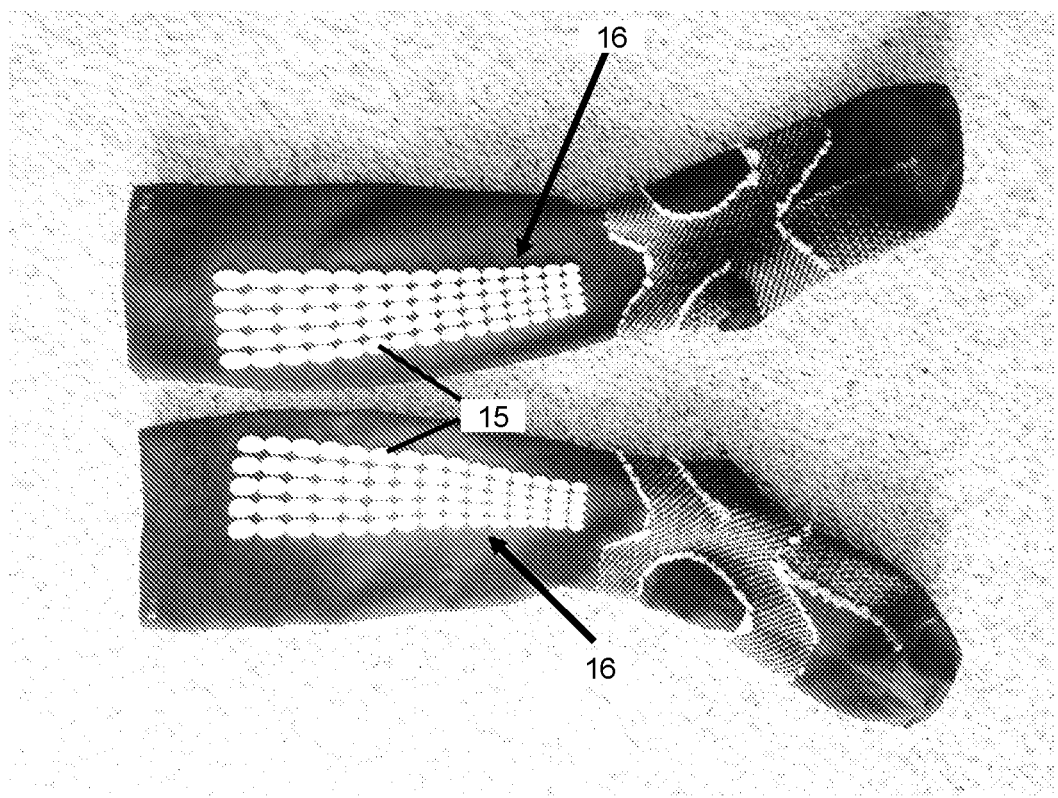
FIG. 7 is a photograph of a pair of socks according to the invention, turned inside-out, and showing the side of the sock that is in contact with the lateral aspect of the leg, in use.
Figure 8:
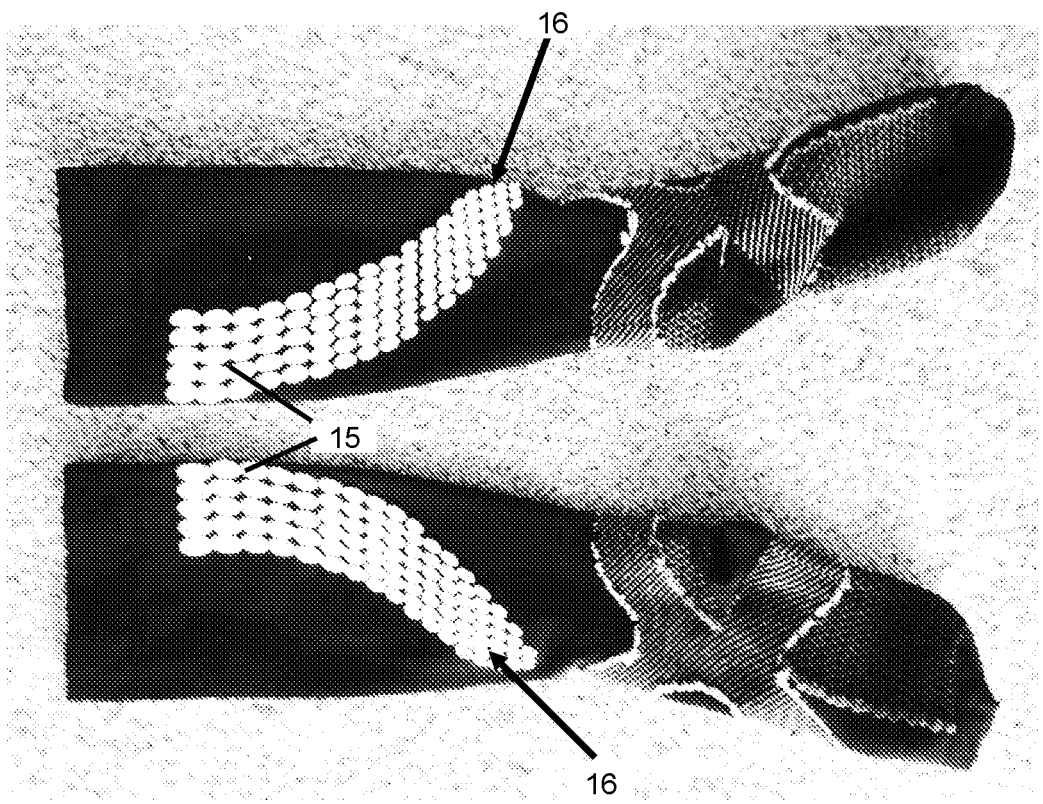
FIG. 8 is a photograph of a pair of socks according to the invention, turned inside-out, and showing the side of the sock that is in contact with the medial aspect of the leg, in use.

As indicated above, FIGS. 7 and 8 are photographs of the insides of a pair of socks, specifically graduated compression socks, having an array of pads that, when worn, provide targeted compression of the saphenous veins. The panel shown in FIG. 7 is adapted to compress the large/great saphenous vein, which is located at the medial aspect of the lower leg. The panel shown in FIG. 8 is adapted to compress the small saphenous vein, which is located at the posterio-lateral aspect of the lower leg (the curve shape follows the position of the vein). Such socks have been tested on a group of athletes in a US club.

The study entailed bleep testing of 12 men and women, all very athletic (playing a number of sports, including baseball, football, basketball etc.), between 16 and 23 years old. Three types of socks were tested, i.e. (A) normal socks, (B) graduated compression socks (as shown in FIGS. 7 and 8 but without pads), and (C) socks as shown in FIGS. 7 and 8.

Testing was undertaken on three separate occasions, each at the same facility and at the same time of night, in order to minimize the effect of environmental factors, and under observed and timed conditions. The participants wore their usual sports socks (A) on day 1, socks (B) on day 2, and, after a day's rest, socks (C) on day 4. They were allowed a warm-up session of 10 minutes after which they underwent a 20 m bleep test, while wearing a F2 polar monitor which recorded the wearer's average and maximum pulse.

The bleep test was downloaded from an APP, and broadcast via speakers so that it was audible to all participants. They all pushed themselves to the maximum.

Results were collated from the watches. Predicted $VO_2$ max values were assigned.

Mean rankings according to the Friedman test were: (A) 1.08; (B) 2.25; and (C) 2.67.

Mean values (SD) according to the Wilcoxon test were ranked similarly.

These results show the surprising effect of targeted compression according to the invention.

The invention claimed is:

1. An article of clothing, adapted to be worn against skin comprising
   a first layer of material having a skin facing surface and an outer surface, the first layer of material providing general compression or graduated compression to an area of a body,
   a second layer of material formed as an array attached to the skin facing surface of the first layer of material, the array comprising a plurality of pads or protrusions, wherein the height of the pads or protrusions is between 100 microns and 10 mm and the array is arranged in a predetermined shape having a width of between 1 and 10 cm, such that the array is configured to be positioned over one or more surface veins in the area of the body, and configured to apply an area of targeted compression to at least 20% of a total length of the one or more surface veins, wherein the area of general compression or graduated compression is larger than the area of targeted compression and the array provides a greater level of compression than the area of general compression or graduated compression configured to be applied to the one or more surface veins, which include a cephalic vein, a basilic vein, a short saphenous vein, a long saphenous vein, a specific plexus of veins, a specific lymphatic plexus, a drainage plexus, and a collection of lymphatic vessels.

2. The article of clothing, according to claim 1, wherein the array is configured to apply targeted compression between 60% and 100% of the total length of the one or more surface veins.

3. The article of clothing, according to claim 2, comprising at least one sleeve, adapted to receive an arm, with the array on an interior of the sleeve and extending in a proximal to distal direction, so as to apply targeted compression to at least one of an anterior lateral aspect and an anterior medial aspect of the arm thereby applying targeted compression to at least one of a cephalic vein and a basilic vein respectively.

4. The article of clothing, according to claim 2, comprising at least one leg, adapted to receive at least a portion of a lower limb, with the array on an interior of the leg and extending in a proximal to distal direction, so as to apply targeted compression to least one of a medial aspect and a posterior lateral aspect of the lower limb thereby applying targeted compression to at least one of a long saphenous vein and a short saphenous vein respectively.

5. The article of clothing, according to claim 1, wherein the pads or protrusions in the array are non-uniform in size.

6. The article of clothing, according to claim 5, wherein the array forms an inward bulge, such that the array provides an area of targeted compression, with a region of greatest compression near a center thereof.

7. The article of clothing, according to claim 1, wherein targeted compression is configured to be applied to the area of the body that includes at least one of an arm, a leg, a buttock, a lateral aspect of the hips, and an anterior chest wall overlying a one or more pectoral muscle.

8. The article of clothing, according to claim 1, wherein the graduated compression is configured to be applied with greater compression to a skin area more distal to the heart and lesser compression to a skin area more proximal to the heart.

9. A device, adapted to be worn against skin for enhancing athletic ability by compressing one or more surface veins thereby increasing available oxygen to muscles, comprising:
   a first layer of material, having a skin facing surface and an outer surface, which provides a region of general compression or graduated compression to skin over one or more surface veins,
   a second layer of material, formed as an array attached to the skin facing surface of the first layer of material, the array comprising a plurality of pads or protrusions, wherein the height of the pads or protrusions is between 100 microns and 10 mm and the array is arranged in a predetermined shape having a width of between 1 and 10 cm and configured to apply a greater level of compression targeted to at least 20% of a total length of the one or more surface veins under skin, which include a cephalic vein, a basilic vein, a short saphenous vein, a long saphenous vein, a specific plexus of veins, a specific lymphatic plexus, a drainage plexus, and a collection of lymphatic vessels.

10. The device, according to claim 9, wherein the array is configured to apply targeted compression between 60% and 100% of the total length of the one or more surface veins.

11. The device, according to claim 10, comprising a shirt with at least one sleeve, configured to receive an arm, wherein the array is arranged in a proximal to distal direction within the sleeve to apply a greater level of compression targeted to at least one of an anterior lateral aspect and an anterior medial aspect of the arm thereby applying a greater level of compression targeted to at least one of the cephalic vein and the basilic vein respectively.

12. The device, according to claim 10, comprising one or more of trousers, leggings, socks, shorts, and tights with at least one leg, configured to receive at least a portion of a lower limb, in which the array is arranged in a proximal to distal direction to apply a greater level of compression targeted to at least one of a medial aspect and a posterior lateral aspect of a lower limb thereby applying a greater level of compression targeted to at least one of a long saphenous vein and a short saphenous vein respectively.

13. The device, according to claim 9, wherein the pads or protrusions in the array are non-uniform in size.

14. The device, according to claim 13, wherein the pads or protrusions form a bulge near a center of the array, such that the compression is greater near the center of the array.

15. The device, according to claim 9, wherein the graduated compression is configured to be applied with greater compression to a skin area more distal to the heart and lesser compression to a skin area more proximal to the heart.

16. A device, adapted to be worn against skin for enhancing athletic ability by compressing one or more surface veins thereby increasing available oxygen to muscles, comprising:
 a first layer of material, having a skin facing surface and an outer surface, which provides a region of general compression or graduated compression to skin over one or more surface veins,
 a second layer of material, formed as an array attached to the skin facing surface of the first layer of material, the array comprising a plurality of pads or protrusions, wherein the pads or protrusions are non-uniform in size and the array is arranged in a predetermined shape having a width of between 1 and 10 cm and configured to apply a greater level of compression targeted to at least 20% of a total length of the one or more surface veins under skin, which include a cephalic vein, a basilic vein, a short saphenous vein, a long saphenous vein, a specific plexus of veins, a specific lymphatic plexus, a drainage plexus, and a collection of lymphatic vessels.

17. The device, according to claim 16, wherein the pads or protrusions form a bulge near a center of the array, such that the compression is greater near the center of the array.

* * * * *